(12) United States Patent
Gresham

(10) Patent No.: US 8,092,423 B2
(45) Date of Patent: Jan. 10, 2012

(54) LOW PROFILE INSTRUMENT ACCESS DEVICE

(75) Inventor: Richard D. Gresham, Guilford, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 0 days.

(21) Appl. No.: 12/964,842

(22) Filed: Dec. 10, 2010

(65) Prior Publication Data

US 2011/0077597 A1    Mar. 31, 2011

Related U.S. Application Data

(63) Continuation of application No. 12/468,153, filed on May 19, 2009, now Pat. No. 7,850,667.

(60) Provisional application No. 61/076,170, filed on Jun. 27, 2008.

(51) Int. Cl.
*A61M 31/00* (2006.01)

(52) U.S. Cl. ........... 604/103; 600/154; 604/96.01; 604/154; 604/323; 604/506

(58) Field of Classification Search ............ 600/154; 604/96.01, 164.03, 164.04, 164.1, 167.03, 604/323, 103, 506
See application file for complete search history.

(56) References Cited

U.S. PATENT DOCUMENTS

| | | | |
|---|---|---|---|
| 5,002,557 A | 3/1991 | Hasson | |
| 5,147,316 A | 9/1992 | Castillenti | |
| 5,176,648 A * | 1/1993 | Holmes et al. | 604/180 |
| 5,215,531 A | 6/1993 | Maxson et al. | |
| 5,226,890 A | 7/1993 | Ianniruberto et al. | |
| 5,257,973 A | 11/1993 | Villasuso | |
| 5,263,939 A | 11/1993 | Wortrich | |
| 5,364,367 A * | 11/1994 | Banks et al. | 604/174 |
| 5,443,484 A | 8/1995 | Kirsch et al. | |
| 5,490,843 A * | 2/1996 | Hildwein et al. | 604/164.03 |
| 5,653,718 A * | 8/1997 | Yoon | 606/148 |
| 5,683,378 A * | 11/1997 | Christy | 606/1 |
| 5,716,662 A | 2/1998 | Fitzburgh | |
| 5,817,061 A | 10/1998 | Goodwin et al. | |
| 5,817,062 A | 10/1998 | Flom et al. | |

(Continued)

FOREIGN PATENT DOCUMENTS

EP    1629787    3/2006

(Continued)

OTHER PUBLICATIONS

European Search Report, Application No. EP 09 25 1620, dated Oct. 16, 2009.

*Primary Examiner* — Jackie Ho
*Assistant Examiner* — Gerald Landry, II

(57) ABSTRACT

A low profile surgical access device includes an elongated cannula having an opening defined at a proximal end thereof including an inner peripheral surface dimensioned to facilitate passage of instrumentation therethrough and an outer peripheral surface configured to operatively engage and removably secure to tissue via, e.g., fixation ribs, adhesive, anchors, clips, suction elements, expandable materials and/or combinations thereof. A valve is operatively coupled to the elongated cannula and provides a substantially fluid tight seal when instrumentation is inserted through the cannula. A seal housing is included which is positionable relative to the cannula and which is configured to operatively engage and removably secure to tissue. The instrument seal in the seal housing is positioned in vertical registry with the valve in the elongated cannula.

11 Claims, 5 Drawing Sheets

U.S. PATENT DOCUMENTS

| | | | |
|---|---|---|---|
| 5,855,566 A | 1/1999 | Dunlap et al. | |
| 5,879,333 A | 3/1999 | Smith | |
| 5,895,377 A | 4/1999 | Smith et al. | |
| 5,911,714 A | 6/1999 | Wenstrom, Jr. | |
| 5,928,198 A | 7/1999 | Lester | |
| 5,935,107 A | 8/1999 | Taylor et al. | |
| 6,159,182 A * | 12/2000 | Davis et al. | 604/167.06 |
| 6,171,299 B1 | 1/2001 | Bonutti | |
| 6,228,063 B1 * | 5/2001 | Aboul-Hosn | 604/174 |
| 6,302,873 B1 * | 10/2001 | Moenning | 604/506 |
| 6,344,038 B1 | 2/2002 | Weber | |
| 6,423,036 B1 | 7/2002 | Van Huizen | |
| 6,432,085 B1 | 8/2002 | Stellon et al. | |
| 6,500,170 B2 | 12/2002 | Palmer et al. | |
| 6,592,573 B2 | 7/2003 | Castaneda et al. | |
| 6,666,846 B1 | 12/2003 | Turovskiy et al. | |
| 6,916,310 B2 | 7/2005 | Sommerich | |
| 6,916,331 B2 * | 7/2005 | Mollenauer et al. | 606/213 |
| 6,923,783 B2 | 8/2005 | Pasqualucci | |
| 6,989,003 B2 | 1/2006 | Wing et al. | |
| 7,011,314 B2 | 3/2006 | McFarlane | |
| 7,011,647 B2 | 3/2006 | Purdy et al. | |
| 7,070,586 B2 | 7/2006 | Hart et al. | |
| 7,115,114 B2 | 10/2006 | Caizza | |
| 7,367,960 B2 | 5/2008 | Stellon et al. | |
| 7,641,648 B2 * | 1/2010 | Bouphavichith et al. | 604/533 |
| 2002/0026207 A1 * | 2/2002 | Stellon et al. | 606/185 |
| 2003/0045834 A1 | 3/2003 | Wing et al. | |
| 2004/0092862 A1 * | 5/2004 | Pasqualucci | 604/27 |
| 2005/0261661 A1 * | 11/2005 | McFarlane | 604/506 |
| 2007/0106319 A1 | 5/2007 | Au et al. | |
| 2008/0306442 A1 | 12/2008 | Bardsley et al. | |
| 2009/0163862 A1 | 6/2009 | Kauphusman et al. | |
| 2009/0182279 A1 | 7/2009 | Wenchell et al. | |

FOREIGN PATENT DOCUMENTS

| | | |
|---|---|---|
| WO | 96/36283 | 11/1996 |
| WO | 2007006306 | 1/2007 |
| WO | 2007093957 | 8/2007 |

* cited by examiner

LOW PROFILE INSTRUMENT ACCESS DEVICE

CROSS REFERENCE TO RELATED APPLICATIONS

This application is a continuation of U.S. application Ser. No. 12/468,153, filed May 19, 2009, now U.S. Pat. No. 7,850,667 which claims the benefit of and priority to U.S. Provisional Application No. 61/076,170, filed Jun. 27, 2008. The disclosures of which are hereby incorporated by reference in its entirety.

BACKGROUND

1. Technical Field

The present disclosure relates to valve system adapted to permit the introduction of surgical instrumentation into a patient's body. More particularly, the present disclosure relates to a low profile valve system for use with an introducer which is intended for insertion into a patient's body and to receive an instrument in sealing engagement therewith.

2. Description of the Related Art

The term "laparoscopy" typically includes a variety of surgical procedures involving one or more remotely operated surgical instruments which are inserted through the interior of the abdomen through one or more surgical incisions to access the operating cavity. "Endoscopic" procedures involve accessing hollow viscera of the body through one or more narrow tubes or cannula inserted through a small entrance incision in the skin. Laparoscopic and endoscopic procedures generally require that any instrumentation inserted into the body be sealed to limit the possibility of infection and to maintain the operating cavity insufflated (if needed). Moreover, laparoscopic and endoscopic procedures often require the surgeon to act on organs, tissue, and vessels far removed from the incision, thereby requiring that any instruments used in such procedures be relatively long and narrow.

For such procedures, the introduction of a tube into certain anatomical cavities such as the abdominal cavity is usually accomplished by use of a trocar assembly made up of a cannula assembly and an obturator assembly. Since the cannula assembly provides a direct passage for surgical instrumentation from outside the patient's body to access internal organs and tissue, it is important that the cannula assembly maintain a relatively gas-tight interface between the abdominal cavity and the outside atmosphere. The cannula assembly generally includes a cannula attached to a cannula housing containing a seal assembly adapted to maintain a seal across the opening of the cannula housing.

Since surgical procedures in the abdominal cavity of the body require insufflating gases to raise the cavity wall away from vital organs, the procedure is usually initiated by use of a so-called Verres needle through which a gas such as $CO_2$ is introduced into the body cavity, thereby creating a pneumoperitoneum. The gas provides a positive pressure which raises the inner body wall away from internal organs, thereby providing the surgeon with a region within which to operate thereby avoiding unnecessary contact with the organs during surgery. An obturator or trocar is inserted into the cannula assembly and used to puncture the abdominal wall. Following removal of the obturator or trocar from the cannula assembly, laparoscopic or endoscopic surgical instruments may be inserted through the cannula assembly to perform surgery within the abdominal cavity. Without the obturator assembly to block the flow of insufflation gas out from the cavity, other structure must be provided to maintain a relatively fluid-tight interface between the abdominal cavity and the outside atmosphere.

Generally in the context of insufflatory surgical procedures a substantially fluid-tight seal is necessary at all times, e.g., during instrument insertion, during instrument manipulation, during instrument immobility (i.e., when an instrument is idle or not being manipulated by the surgeon or technician) and when an instrument is not present in the cannula. In certain cases, the height of the valve system relative to the patient skin may cause interference with the surgeon's ability to manipulate the instrument within the operating cavity which may in some cases cause a disruption or interference with the fluid-tight seal resulting in relative deflation of the pneumoperitoneum (in the minor instance) to contamination of the operating cavity (in a critical instance).

As a result, attempts have been made to improve the overall seal in conjunction with a cannula assembly to maintain the integrity of the seal between the body cavity and the atmosphere outside the patient's body. However, such systems to date have failed to address the full range of surgeons' needs against the potential risks they propose when manipulating instruments within tight operating cavities. A need also exists for surgical devices and methods which anchor a cannula and instrument support housings (or other access member) to a patient with minimum tissue trauma while still providing a positive seal.

SUMMARY

In accordance with one particular embodiment of the present disclosure, a low profile surgical access device includes an elongated cannula having an opening defined at a proximal end thereof including an inner peripheral surface dimensioned to facilitate passage of instrumentation therethrough and an outer peripheral surface configured to operatively engage and removably secure to skin tissue via, e.g., fixation ribs, adhesive, anchors, clips, suction elements, expandable materials and/or combinations thereof. A valve is operatively coupled to the elongated cannula for providing a substantially fluid tight seal when instrumentation is inserted through the cannula.

A seal housing is included which is selectively positionable relative to the cannula and configured to operatively engage and removably secure to skin tissue via, e.g., an adhesive, anchors, clips, suction and/or combinations thereof. The seal housing includes an instrument seal for insertion of instrumentation therethrough which is selectively positionable in vertical registry with the valve in the elongated cannula.

In one embodiment, the proximal end of the cannula includes a flange which mechanically engages and secures the cannula to tissue. In another embodiment, the cannula includes an obturator or trocar that is removably disposed therethrough which is configured to puncture tissue for accessing the operating cavity. The cannula may also include a dilator operatively associated therewith for facilitating delivery of the cannula and removal of the trocar.

In another embodiment, the cannula is secured utilizing an expandable material disposed within a port defined within the outer peripheral surface of the cannula. The expandable material is selectively deployable via one or more nozzles disposed through the cannula and exposed on an outer surface of the flange. Pressure or gas is supplied through the nozzle to inflate the expandable material and secure the cannula to the underside of the skin tissue.

In still another embodiments, the valve may consist of zero closure valves, zero seal valves, duck bill valves, single-slit valves, multiple slit valves, trumpet valves and flapper valves. Yet in another embodiment, the cannula or the seal housing is secured utilizing suction elements configured as microscopic needle-like barbs which minimally pierce only the outermost layer of the epidermis to secure the cannula or the seal housing to the skin tissue.

The present disclosure also relates to a method for providing a low profile surgical access port for surgical instrumentation and includes the initial step of providing a cannula having an elongated tube with an opening defined at a proximal end thereof having an inner peripheral surface dimensioned to facilitate passage of instrumentation therethrough. The cannula also includes an outer peripheral surface configured to operatively engage and removably secure to skin tissue. A valve is included which operatively couples to the cannula and provides a substantially fluid tight seal when instrumentation is inserted through the cannula. The providing step of the method also includes providing an instrument seal housing having an instrument seal disposed therein for fluid-tight insertion of instrumentation therethrough.

The method also includes the steps of: introducing the cannula into an operating cavity to create a passageway for surgical instrumentation and removably securing the cannula via fixation ribs, adhesive, anchors, clips, suction elements, expandable materials and/or combinations thereof; positioning the instrument seal housing relative to the cannula such that the instrument seal is positioned in substantial vertical registry with the valve in the cannula; and removably securing the seal housing to skin tissue via an adhesive, anchors, clips, suction elements and/or combinations thereof.

BRIEF DESCRIPTION OF THE DRAWINGS

The objects and features of the present disclosure are set forth with particularity in the appended claims. The present disclosure, both as to its organization and manner of operation, together with further objectives and advantages, may be best understood by reference to the following description, taken in connection with the accompanying drawings, as set forth below, wherein:

DETAILED DESCRIPTION

Figure 1:
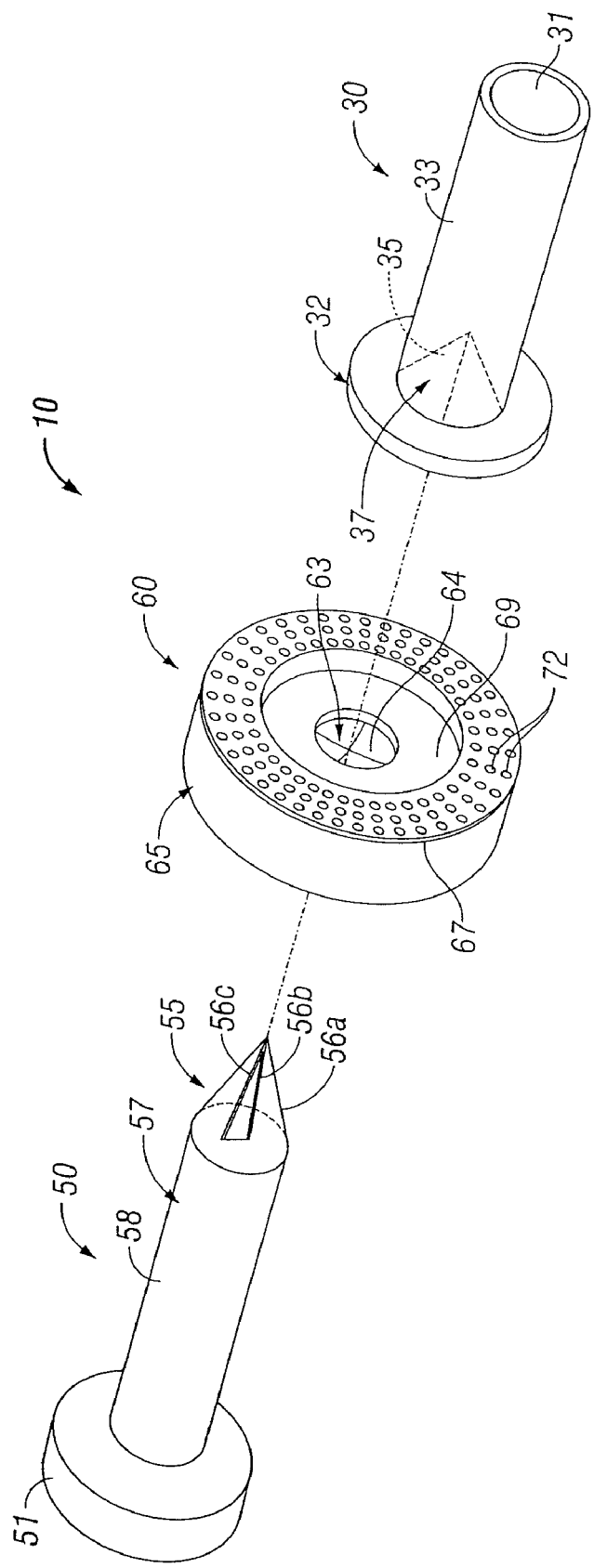
FIG. 1 is an perspective view with parts separated of a low profile instrument access device according to one embodiment of the present disclosure showing a cannula, trocar and instrument seal housing.

Methods and surgical devices described herein with respect to the present disclosure are directed towards providing access to a body cavity for surgical procedures. Specifically, methods and devices of the present disclosure substantially prevent substantial loss of fluids through an incision by providing a low profile access assembly that can form a peripheral seal against the incision and anchor the access assembly to the body, while allowing surgical instruments to more easily access the interior of the body during minimally invasive surgical procedures at greater angles to reach difficult organs.

To access a desired cavity, the cannula is inserted through a percutaneous opening in the patient's body, such as an incision through the abdominal wall made by a trocar. The cannula must typically pass through the abdominal wall which includes the outer skin, a layer of fat, a layer of fascia or alternating muscle and fascia, and the peritoneum. The layers of fat and fascia may vary in thickness, depending upon the body location and whether the patient is asthenic or obese. The peritoneum is a strong, elastic membrane lining the walls of the abdominal cavity. Just below the peritoneum, lie several vital organs, such as the liver, stomach and intestines, and other sensitive tissues. This is typically the area that the access assembly is positioned to reach.

To perform any given surgical procedure in this area, the abdominal wall is typically gently elevated relative to these vital organs by inflating the area with an insufflation gas such as carbon dioxide. This provides sufficient operating space for a surgeon to maneuver surgical instruments within the anatomical cavity or so-called "pneumoperitoneum". To prevent loss of this insufflation gas and loss of operating space, the cannula must provide a gas-tight seal against the abdominal wall while permitting a sufficient range of motion for the instruments. In addition, the gas tight seal must cause as minimal damage as possible to the engaged abdominal tissue.

Although the present disclosure is described with reference to a surgical procedure which includes a penetration of the abdominal wall, such description is made for illustrative and exemplary purposes. As those skilled in the art will appreciate, many other surgical procedures may be performed by utilizing the methods and materials described herein. Particular embodiments of the presently disclosed low profile access device, cannula, anchor and methods of using the foregoing will now be described in detail with reference to the figures, in which like reference numerals identify corresponding elements throughout the several views.

Turning now to the various figures which show envisioned devices for use with the present disclosure, one embodiment of a low profile instrument access device is shown in FIG. 1 with parts separated and is generally designated as access device 10. More particularly, access device 10 includes three main component elements or pieces, namely, cannula 30, trocar 50 and seal housing 60 which mutually cooperate to create a low profile access port 10 for various introduction of surgical instrumentation into an operating cavity. Each of these main components (i.e., cannula 30, trocar 50 and seal housing 60) is explained in detail below along with some explanation of the intra-operative relationship between working components where appropriate.

Cannula 30 includes an elongated tube 30a having an inner periphery 31 defined therein dimensioned to facilitate insertion of the trocar 50 and various other surgical instrumentation (not shown) therethrough. One or more surgical lubricants, highly polished surfaces or reduced-friction surfaces may be employed to further facilitate this purpose as is known in the art. A proximal end 34 of the elongated tube 30a includes an opening 37 disposed in fluid communication with the inner periphery 31 separated by a so-called "zero closure valve" or "zero seal" 35 which tapers distally and inwardly to a sealed configuration as shown in the FIG. 1. Valve 35 opens to permit passage of surgical instrumentation (not shown) therethrough and closes in the absence thereof and is configured to particularly remain closed upon exposure to the internal pressures associated with insufflation. Other types of zero closure valves are also contemplated including duck bill valves, single or multiple slit valves, trumpets valves, flapper valves, etc.

Figure 2A:
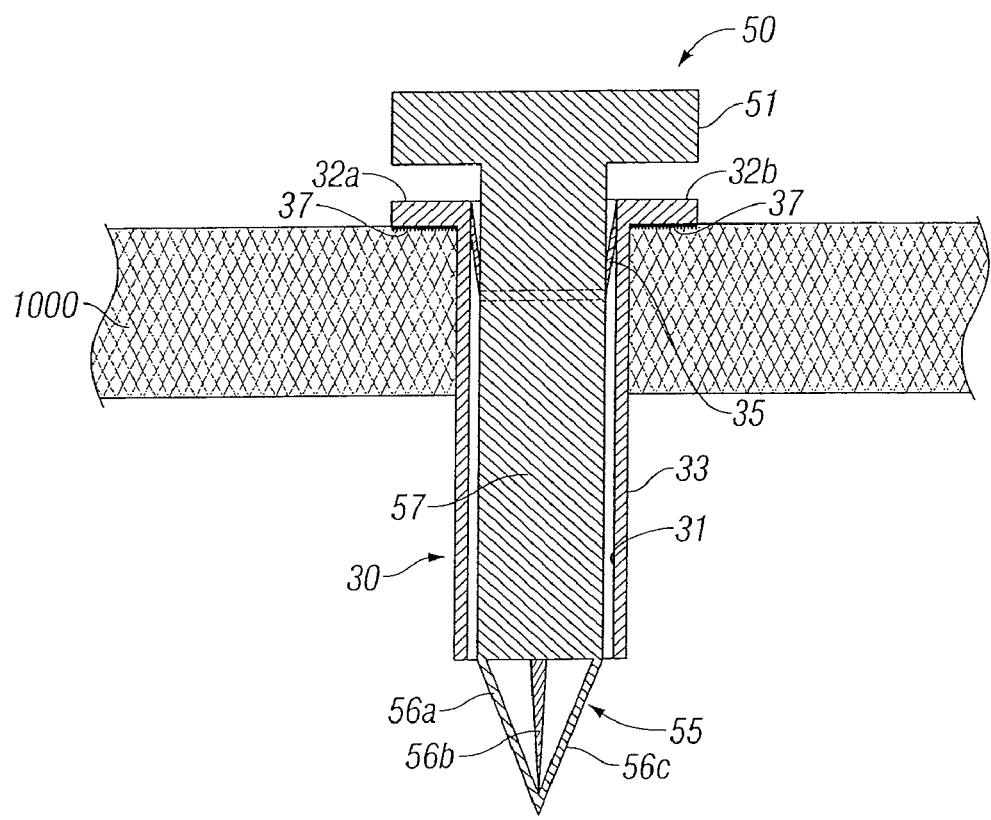
FIG. 2A is a schematically-illustrated, front view of the cannula and trocar in an assembled configuration being introduced into an operating cavity and creating a passageway therein for surgical instrumentation.

The proximal end 34 of elongated tube 30a also includes a flange ring 32 (or side flanges 32a and 32b when shown in cross section) which is configured to operatively engage and secure the cannula 30 to skin tissue 1000 (See FIG. 2A). Flange 32 is designed to extend beyond the periphery of tube 30a to stabilize the cannula 30 atop skin tissue and provide adequate surface area to insure secure engagement of the cannula 30 to the skin tissue 1000 to avoid unintentional disengagement of the cannula 30 during operating conditions. FIGS. 2A-2E show various envisioned mechanical mechanisms for securing the cannula 30 to the skin tissue 1000 and are explained in more detail below with reference to these figures.

For the purposes herein and for simplicity purposes, trocar 50 is generally described to merely include the basic operating elements of the trocar 50 without referring to the variety of different operating features and accessories commonly known in the industry, e.g., dilators, interchangeable tips, interchangeable seals, stopcocks, optical ports, closure devices, reducers, shields, sheaths, etc. More particularly, trocar 50 includes a user end 51 disposed at a proximal end thereof and an operating tip 55 disposed at a distal end thereof separated by an elongated shaft 57 disposed therebetween. The outer periphery 58 of shaft 57 is dimensioned for sliding engagement within inner periphery 31 of cannula 30 as explained above. The operating tip 55 includes three sharpened edges 56a-56c which, together, cooperate to pierce tissue 1000 and facilitate introduction of the trocar 50 and cannula 30 into the operating cavity as best seen in FIG. 2A. Other types of operating tips (not shown) are also envisioned which may be suitable for different surgical purposes.

Seal housing 60 includes is generally ring-like and includes an outer ring 65 (composed of left and right sections 65a and 65b, respectively, at cross section) and an inner ring 69 which defines an opening 63 having a seal 64 supported therein. Seal 64 is configured to facilitate passage of surgical instrumentation (not shown) therethrough and is configured to remain closed upon exposure to the internal pressures associated with insufflation. As such, seal 64 may be any one of the above-identified valves, e.g., zero closure valve zero seal, duck bill valve, single or multiple slit valve, trumpets valve, flapper valve, etc.

The tissue engaging surface 67a and 67b of each outer ring section 65a and 65b, respectively, includes an adhesive or other suitable material 72 which secures the seal housing 60 to the skin tissue 1000. Other mechanical devices may be utilized to accomplish this purpose and are explained below with particular reference to FIGS. 4A-4C.

In use, the surgeon initially assembles the cannula 30 and trocar 50 by introducing the trocar 50 into and through the inner peripheral surface 31 of the cannula 30 such that the operating tip 55 extends from the distal end of the elongated tube 30a. The cannula 30 and trocar 50 assembly is now ready to create a passageway into the operating cavity to facilitate the introduction and withdrawal of instrumentation while maintaining a safe, sterile and fluid tight interface between the operating cavity and the surrounding surgical atmosphere. Once pierced, the trocar 50 may be easily withdrawn from the cannula 30 without losing the integrity of the fluid tight interface.

As mentioned above, FIGS. 2A-2E show various envisioned mechanical mechanisms which are designed to removably secure the cannula 30 to the skin tissue 1000 after introduction of the cannula 30 utilizing the cannula 30 and trocar 50 assembly as explained above. For example, FIG. 2A shows the use of an adhesive or other suitable compound 37 which may be disposed on the tissue engaging side of the outwardly extending flange ring 32 (or flanges 32a and 32b as shown in cross section of FIG. 2A) of the cannula 30. During introduction of the cannula 30, the underside of flanges 32a and 32b are forced to engage the skin tissue 1000 such that the adhesive 37 is held in contact with the tissue 1000 long enough to cure or set and hold the cannula 30 securely in place against the tissue until desired removal. The trocar 50 may then be removed without effecting the position of the cannula 30.

Figure 2B:
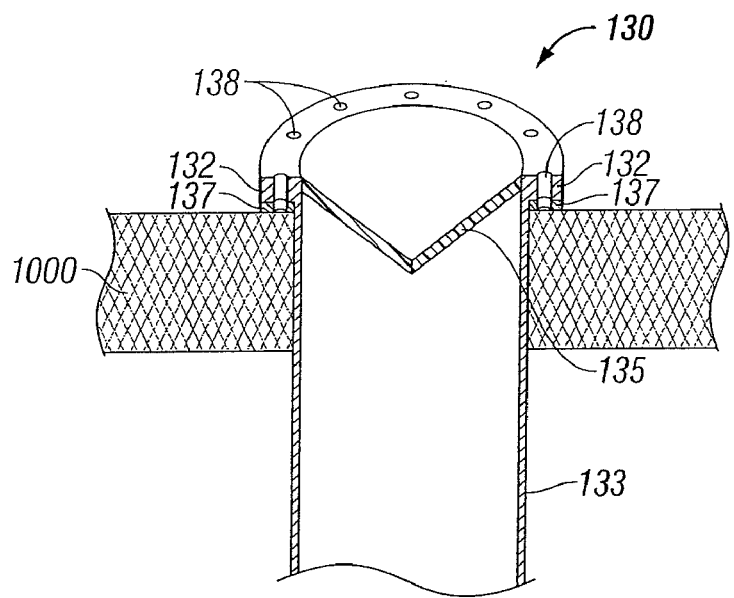
FIG. 2B is schematically-illustrated, perspective view of another embodiment of a cannula having a suction element for securing the cannula to skin tissue.

FIG. 2B shows another envisioned embodiment wherein the cannula 130 is secured to the skin tissue 1000 utilizing negative pressure or suction. One or more deformable membranes 137 are positioned on the underside (or tissue engaging side) of the flange ring 132 in fluid communication with a nozzle or fill port 138. Once the trocar 50 introduces the cannula 30 into the operating cavity and the trocar 50 is removed through seal 135 of cannula 130, air under the flange ring 132 is withdrawn through the nozzles 138 thereby creating negative pressure between the flange ring 132 the skin tissue 1000 and securing the flange ring 132 to the tissue. Once pressure is normalized under the flange ring 132, the cannula 130 may be easily removed from the skin tissue 1000.

Figure 2C:
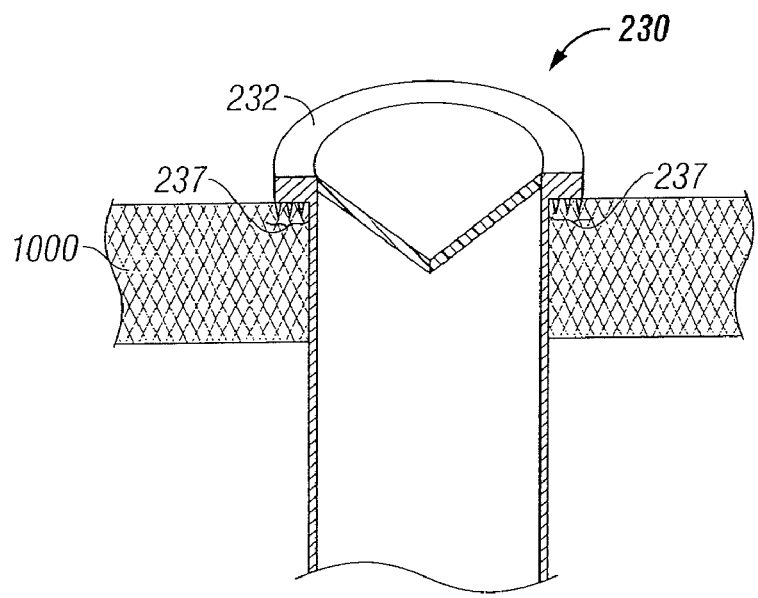
FIG. 2C is schematically-illustrated, perspective view of another embodiment of a cannula having a series of mechanical barbs for securing the cannula to skin tissue.

FIG. 2C shows another embodiment of a cannula 230 which includes a series of traumatic teeth-like barbs which protrude from the underside of the flange ring 232 to engage tissue 1000. During introduction of the cannula 230 and trocar 50 assembly into the operating cavity to create the instrument passageway, the barbs 237 are forced into engagement with the tissue 1000 thereby maintaining the cannula 230 securely in place against the tissue 1000 until removal. The barbs 237 may be configured as microscopic needles (so-called "microneedles") to minimally pierce only the outermost layers of the epidermis while still sufficiently securing the cannula 230 in place atop the skin tissue 1000 without causing undue trauma to the patient's skin.

In alternative instances, it may be necessary to use longer barbs which do pierce the epidermal layers of the skin to properly secure the cannula 230 in place atop the skin tissue 1000. The barbs 237 may also be configured as blunt hollow tube-like projections (not shown) which act like tiny suction cups which create a positive seal against the skin tissue 1000 when pressure is applied, e.g., during introduction of the cannula 230 into the operating cavity.

Figure 2D:
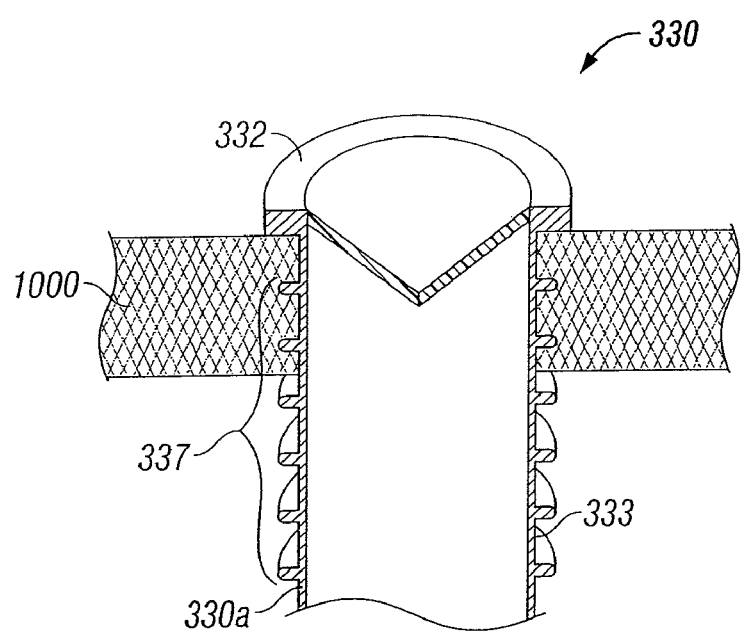
FIG. 2D is schematically-illustrated, perspective view of another embodiment of a cannula having fixation ribs for securing the cannula to skin tissue.

FIG. 2D shows yet another embodiment of a cannula 330 which includes a series of ribbed projections 337 that project from the outer peripheral surface 333 of the elongated tube 330a and which are configured to engage the skin tissue 1000. More particularly, upon insertion of the cannula 330 and trocar 50 assembly into the operating cavity, the surgeon forces the trocar 50 into the tissue 1000 and forces the cannula 330 into the operating cavity as far as possible such that the proximal-most rib 337 wedges against the underside of the skin tissue 1000. As a result thereof, skin tissue 1000 is biased between the flange ring 332 and the proximal-most rib to secure the cannula 330 atop the skin tissue 1000. The ribs 337 (e.g., a top side thereof) may be made from material having a high coefficient of friction to enhance the fluid tight seal between the cannula 330 and the skin tissue 1000 and maintain the cannula 330 in tight, secure engagement during surgical conditions and reduce the chances of slippage.

Alternatively, the outer ribs 337 may be arranged in a helical fashion (not shown) on the outer peripheral surface 333 of the elongated tube 330a which would allow the surgeon to rotate or screw the cannula 330 in a given direction to further secure and/or release the cannula 330. The ribs 337 may be utilized in combination with one or more of the other mechanical devices described herein to enhance the engagement of the cannula 330 with the skin tissue 1000.

Figure 2E:
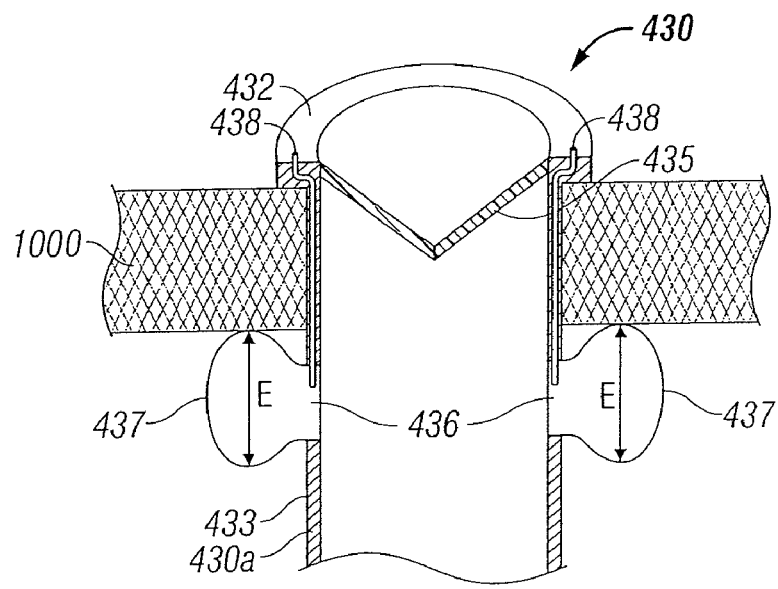
FIG. 2E is schematically-illustrated, perspective view of another embodiment of a cannula having an expandable membrane for securing the cannula to skin tissue.

FIG. 2E shows yet another embodiment of a cannula 430 which includes a selectively inflatable anchoring balloon 437 which is configured to deploy from the outer peripheral surface 433 of the elongated tube 430a after insertion of the cannula 430 into the operating cavity and secure the cannula 430 to the skin tissue 1000. More particularly, upon insertion of the cannula 430 and trocar 50 assembly into the operating cavity, the surgeon forces the trocar 50 into the tissue 1000 and forces the cannula 330 into the operating cavity as far as possible such that a deployment port 436 defined in the outer peripheral surface 433 of elongated tube 430a clears the underside of the skin tissue 1000. Once cleared (and typically prior to removal of the trocar 50), the surgeon introduces air or gas into a nozzle 438 disposed on the outer-facing side of flange ring 432 which activates and deploys a balloon or other type of expandable member 437 to inflate in the direction "E" and extend beyond the outer peripheral surface 433 of elongated tube 430a.

As a result thereof, skin tissue 1000 is wedged between the flange ring 432 and the balloon 437 to secure the cannula 430 atop the skin tissue 1000. The balloon 437 may be inflated/deflated as desired to enhance/reduce the fluid-tight seal or the balloon 437 maybe utilized in combination with one or more of the other mechanical devices described herein to enhance the engagement of the cannula 430 with the skin tissue 1000. Once the cannula 430 is secured in this instance, the trocar 50 is removed though seal 435.

After the cannula, e.g., cannula 30, is positioned and secured atop the skin tissue 1000 and the trocar 50 is removed, the instrument seal housing 60 is positioned relative to the cannula 30 to facilitate the introduction of various surgical instrumentation (not shown) into and out of the operating cavity under sterile operating conditions while maintaining a substantially fluid tight seal between the operating cavity and the atmospheric conditions.

Figure 3:
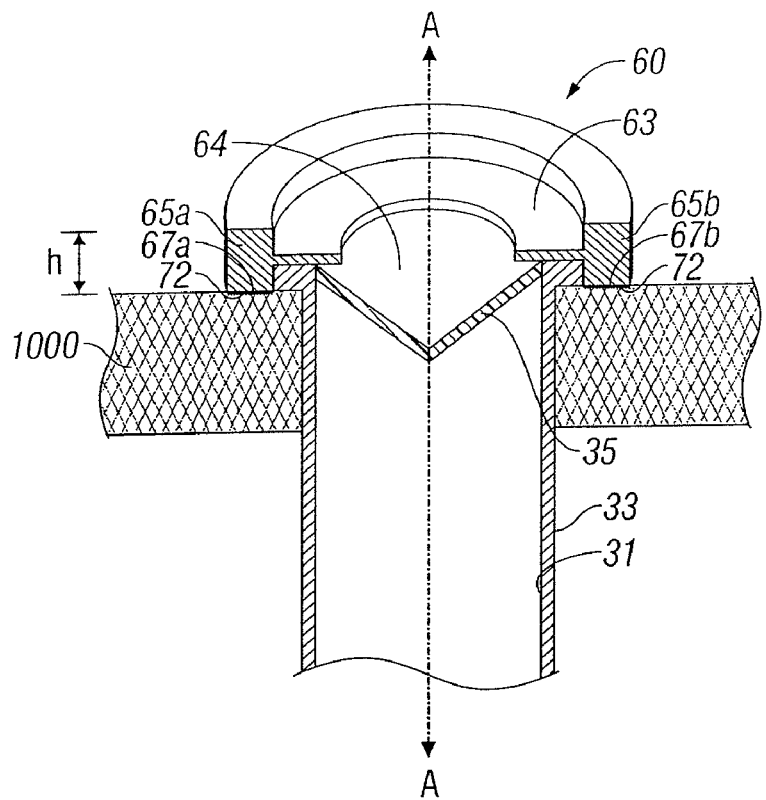
FIG. 3 is a schematically-illustrated, front view showing the low profile instrument access device assemble for operation atop skin tissue with the seal housing and the cannula spaced relative to one another and separately and independently engaged to skin tissue.

As best shown in FIG. 3, seal housing 60 is positioned in a concentric fashion about cannula 30 such that seal 64 and seal 35 align in substantial vertical registry along an imaginary axis A-A disposed therethrough. In this manner, flanges 32a and 32b remain concentrically spaced from the tissue engaging surfaces 67a and 67b of sections 65a and 65b, respectively, and the seal housing 60 and the cannula 30 do not operatively engage one another in any fashion but, in fact, independently attached to different areas of skin tissue 1000. The seal housing 60 and cannula 30 may also be attached to the skin tissue 1000 by the same or different mechanical methods of attachment as detailed below with reference to FIGS. 4A-4C.

Since the cannula 30 is initially introduced and then anchored to the skin tissue 1000 independently of the instrument seal housing 60, the overall head height "h" or profile (See FIG. 3) of the seal housing 60 may be reduced thereby providing the surgeon with a greater range of motion for the surgical instrumentation (less vertical restriction) enabling access to more difficult areas within the operating cavity.

Figure 4A:
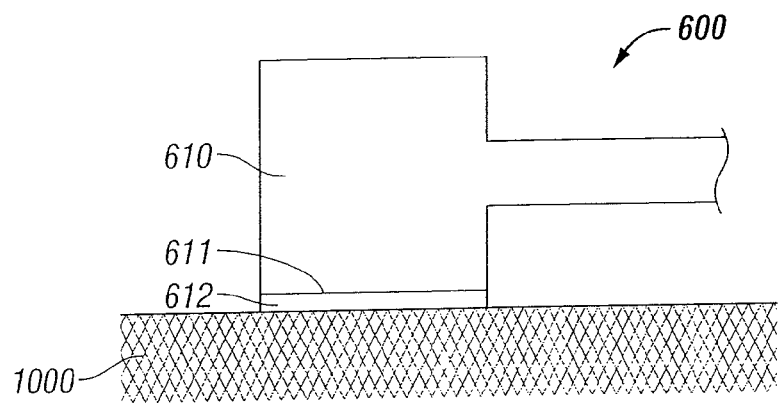
FIG. 4A is a schematically-illustrated, front view of another embodiment of a seal housing with an adhesive for securing the seal housing to skin tissue.

FIG. 4A shows one envisioned seal housing 600 having an outer ring section 610 which is configured to selective engage skin tissue 1000 by virtue of an adhesive or other suitable compound 612 disposed on the tissue engaging surface 611 of section 610. After the cannula 30 is introduced into the operating cavity and secured to the skin tissue 1000 by one or more of the methods described above, the seal housing 600 is then concentrically positioned and spaced relative to the cannula 30 such that the adhesive 612 is held in contact with the tissue 1000 long enough to cure or set and hold the seal housing 600 securely in place against the tissue 1000 until desired removal. Once the seal housing 600 is secured, instruments may be selectively introduced, easily manipulated and removed from within the operating cavity through the seal housing 600 and cannula 30.

Figure 4B:
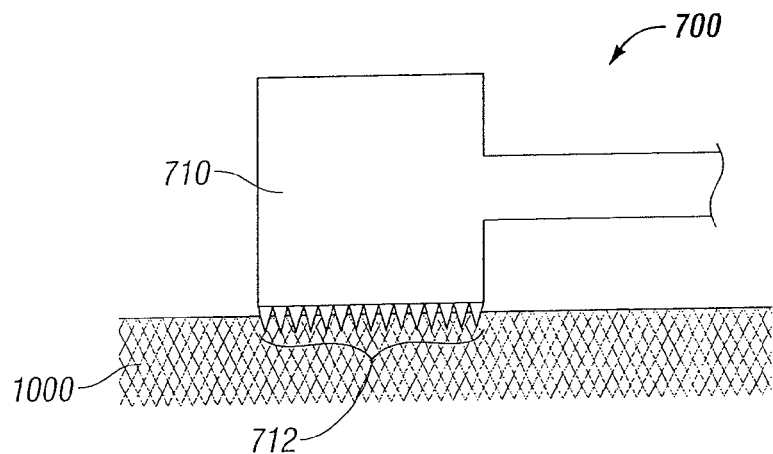
FIG. 4B is schematically-illustrated, perspective view of another embodiment of a seal housing having a series of mechanical barbs for securing the seal housing to skin tissue.

FIG. 4B shows another envisioned seal housing 700 having an outer ring section 710 which is configured to selective engage skin tissue 1000 by virtue of a series of micro-engaging barbs or teeth 712 which upon an application of force or pressure grip the skin tissue 1000 and secure section 710 to the skin tissue 1000 until desired removal, Much like barbs 237, barbs 712 may be configured as microscopic needles (so-called "microneedles") to minimally pierce only the outermost layers of the epidermis while still sufficiently securing the section 710 in place atop the skin tissue 1000 without causing undue trauma to the patient's skin. The barbs 712 may also be configured as tiny, needle-like suction elements or tubes which create a positive seal against the skin tissue 1000 when pressure is applied.

Figure 4C:
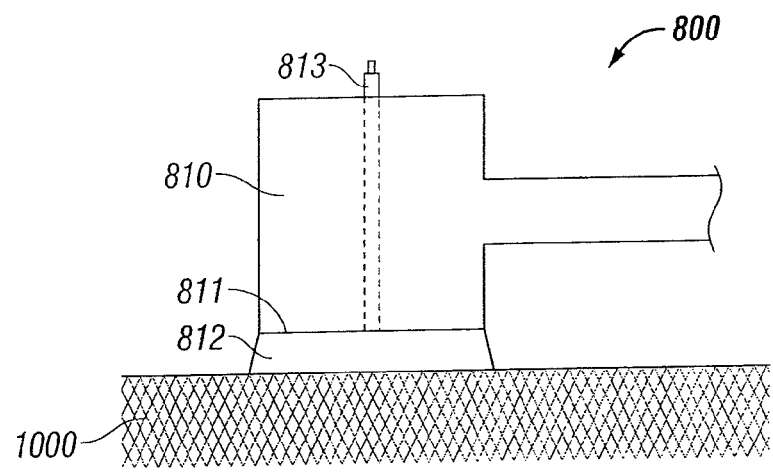
FIG. 4C is schematically-illustrated, perspective view of another embodiment of a seal housing having a suction element for securing the seal housing to skin tissue.

FIG. 4C shows yet another embodiment of an instrument seal housing 800 which includes an outer ring section 810 having a suction element or member 812 disposed on a tissue engaging surface 811 thereof that selectively secures the section 810 to skin tissue 1000. More particularly, once the cannula 30 is properly positioned into the operating cavity, the instrument seal housing 800 is concentrically positioned relative to the cannula 30 such that the suction member 812 engages tissue 1000. A vacuum port or nozzle 813 is operatively coupled to the suction member 812 and removes air under negative pressure (via a suction source (not shown)) to provide a positive seal between the suction member 812 and the skin tissue 1000. Once pressure is normalized under the section 810, the housing 800 may be easily removed from the skin tissue 1000.

The present disclosure also relates to a method for providing a low profile surgical access port for surgical instrumentation and includes the initial step of providing a cannula 30 having an elongated tube 30a with an opening 37 defined at a proximal end 34 thereof including an inner peripheral surface 37 dimensioned to facilitate passage of instrumentation therethrough. The cannula 30 also includes an outer peripheral surface 33 configured to operatively engage and removably secure to tissue and a valve 35 operatively coupled to the cannula 30 which provides a substantially fluid tight seal when instrumentation is inserted through the cannula 30. The providing step of the method also includes providing an instrument seal housing 60 having an instrument seal 63 disposed therein for fluid-tight insertion of instrumentation therethrough.

The method also includes the steps of: introducing the cannula 30 into an operating cavity to create a passageway for surgical instrumentation and removably securing the cannula 30 via fixation ribs, adhesive, anchors, clips, suction elements, expandable materials and/or combinations thereof; positioning the instrument seal housing 60 relative to the cannula 30 such that the instrument seal 63 is positioned in substantial vertical registry with the valve 35 in the cannula 30; and removably securing the seal housing 60 to tissue via an adhesive, anchors, clips, suction elements and/or combinations thereof.

The proximal end 34 of the cannula 30 of the providing step may include a flange 32 which mechanically engages and secures the cannula 30 to tissue 1000. The cannula 30 of the providing step may also include an inner peripheral surface 31 defined therethrough which is configured to slidingly receive a trocar 50 therein for puncturing tissue and introducing the cannula 30 into the operating cavity. A dilator 51 may be operatively associated with the trocar 50 for facilitating introduction of the cannula 30 and removal of the trocar 50.

From the foregoing and with reference to the various figure drawings, those skilled in the art will appreciate that certain modifications can also be made to the present disclosure without departing from the scope of the present disclosure. While the invention has been particularly shown, and described with reference to the particular embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A surgical access device, comprising:
   a cannula including an elongated tube having an inner peripheral surface dimensioned to facilitate passage of instrumentation therethrough and an outer peripheral surface configured to operatively engage and removably secure to tissue; and
   a seal housing positionable around the outer peripheral surface of the cannula and configured to operatively engage and removably secure to tissue, the seal housing including an instrument seal for insertion of instrumentation therethrough, the cannula and the seal housing separately and mechanically engaging tissue;
   wherein a proximal end of the cannula includes a flange that mechanically engages and secures the cannula to tissue, and wherein the cannula is secured utilizing an expandable material disposed within a port defined within the outer peripheral surface of the cannula, the expandable material being selectively deployable via a nozzle disposed through the cannula and exposed on an outer surface of the flange.

2. A surgical access device according to claim 1 further comprising a valve operatively coupled to the cannula, the valve providing a substantially fluid tight seal when instrumentation is inserted through the cannula.

3. A surgical access device according to claim 2, wherein the valve is selected from the group consisting of zero closure valves, zero seal valves, duck bill valves, single-slit valves, multiple slit valves, trumpet valves and flapper valves.

4. A surgical access device according to claim 1, wherein the cannula includes a trocar removably disposed therethrough for puncturing tissue.

5. A surgical access device according to claim 4, wherein the cannula includes a dilator operatively associated therewith for facilitating delivery of the cannula and removal of the trocar.

6. A surgical access device according to claim 1, wherein the outer peripheral surface includes at least one of fixation ribs, adhesive, anchors, clips, suction elements, expandable materials and combinations thereof.

7. A surgical access device according to claim 1, wherein the seal housing includes at least one of an adhesive, anchors, clips, suction and combinations thereof.

8. A surgical access device according to claim 1, wherein at least one of the cannula and the seal housing is secured utilizing suction elements configured as microscopic needle-like barbs which mechanically engage skin tissue.

9. A surgical access device according to claim 8, wherein the microscopic needle-like barbs minimally pierce only the outermost layer of the epidermis to secure at least one of the cannula and the seal housing to skin tissue.

10. A surgical access device, comprising:
    a cannula including an elongated tube having an inner peripheral surface dimensioned to facilitate passage of instrumentation therethrough and an outer peripheral surface configured to operatively engage and removably secure to tissue;
    a seal housing positionable around the outer peripheral surface of the cannula and configured to operatively engage and removably secure to tissue, the seal housing including an instrument seal for insertion of instrumentation therethrough, the cannula and the seal housing separately and mechanically engaging tissue; and
    wherein at least one of the cannula and the seal housing is secured utilizing suction elements configured as microscopic needle-like barbs which mechanically engage skin tissue.

11. A surgical access device according to claim 10, wherein the microscopic needle-like barbs minimally pierce only the outermost layer of the epidermis to secure at least one of the cannula and the seal housing to skin tissue.

* * * * *